United States Patent [19]

Omura

[11] Patent Number: 5,091,441
[45] Date of Patent: Feb. 25, 1992

[54] DENTAL COMPOSITION

[75] Inventor: Ikuo Omura, Kurashiki, Japan

[73] Assignee: Kuraray Co., Ltd., Kurashiki, Japan

[21] Appl. No.: 379,552

[22] Filed: Jul. 13, 1989

[30] Foreign Application Priority Data

Jul. 13, 1988 [JP] Japan ............................ 63-175627

[51] Int. Cl.$^5$ ............................................ C09J 4/00
[52] U.S. Cl. ................................... 523/109; 428/516; 220/903; 523/176; 526/210
[58] Field of Search ............ 523/176, 109; 526/210, 526/212; 428/516

[56] References Cited

U.S. PATENT DOCUMENTS

| | | | |
|---|---|---|---|
| 3,435,012 | 3/1969 | Nordlander | 520/176 |
| 3,661,876 | 5/1972 | Wegenund et al. | 523/176 |
| 3,899,382 | 8/1975 | Matsuda et al. | 523/176 |
| 4,331,580 | 5/1982 | Bunyan | 523/176 |
| 4,431,787 | 2/1984 | Werber | 523/176 |

*Primary Examiner*—Bernard Lipman
*Attorney, Agent, or Firm*—Oblon, Spivak, McClelland, Maier & Neustadt

[57] ABSTRACT

The invention provides dental compositions comprising a radical-polymerizable monomer and an organic peroxide, which are dissolved in a volatile tertiary alochol. Also provided are the compositions packed in a plastic contains, having a long shelf life.

7 Claims, No Drawings

DENTAL COMPOSITION

BACKGROUND OF THE INVENTION

1. Field of the Invention

This invention relates to dental compositions, and more particularly, to dental compositions useful as a primer or an adhesive to be applied to the surface of teeth and/or dental materials to thereby effect adhesion.

2. Description of the Background Art

Solutions of liquid methacrylate monomer and an organic peroxide, such as dibenzoyl peroxide, in a volatile organic solvent, are used in dentistry in adhesives or primers. The problem with these solutions is that they tend to undergo polymerization in storage. Therefore, such solutions are usually kept in containers characterized by high oxygen permeability, such as polyethylene or polypropylene. They are also kept in rather small containers, usually of a volume as small as about 10 cc, to facilitate a constant supply of oxygen gas to the solvents, which prevents the solution from polymerizing. The typical volatile organic solvents used in those solutions such as hydrocarbons, esters and ketones have a relatively low molecular weight and therefore permeate readily through plastics of high oxygen permeability. Therefore, when a solution of a methacrylate monomer diluted with such organic solvent is kept in a plastic container, the organic solvent permeates through the container, resulting in a volume reduction of the solution.

Alcohols, such as ethyl alcohol and isopropyl alcohol are known diluting solvent for dental priming agents or dental adhesives. Although such alcohols do not permeate through the above plastics, they have the drawback that they accelerate the decomposition of the organic peroxides. Compositions of free radical-polymerizable monomers, an organic peroxide, and alcohol, therefore are rapidly reduced in content of organic peroxide, or they tend to solidify due to polymerization. Hence, it has been impossible to store such solutions for extended periods of time. Accordingly, it has been difficult to provide dentists with primers or adhesives of stable compositions of a free radical-polymerizable monomer, organic peroxide, and volatile solvent.

SUMMARY OF THE INVENTION

Accordingly, it is one object of the present invention to provide a dental composition, comprising a free radical-polymerizable monomer, an organic peroxide and a volatile organic solvent (diluting agent).

This and other objects have been achieved by the recognition that certain volatile organic solvents will permeate slowly through plastics having a high oxygen permeability and will result in low organic peroxide decomposition. Tertiary alcohols, in particular, have been found to exceptionally satisfy the needs of this invention.

Thus, the present invention provides dental compositions of a free radical-polymerizable monomer, and an organic peroxide dissolved in a tertiary alcohol which are stored in plastic containers.

DESCRIPTION OF THE PREFERRED EMBODIMENTS

In the present invention, any known free radical-polymerizable monomer can be used. Preferable are (meth)acrylate monomers which are generally used for dental materials.

Examples of such monomers include methyl (meth)acrylate, ethyl (meth)acrylate, 2-hydroxyethyl (meth)acrylate, ethylene glycol di(meth)acrylate, neopentyl glycol di(meth)acrylate, triethylene glycol di(meth)acrylate, 2,2-bis[4-(3-methacryloyloxy-2-hydroxypropoxy)phenyl]propane (abbreviated as Bis-GMA), 2,2-bis[(meth)acryloyoxypolyethoxyphenyl]propane, trimethylolpropane tri(meth)acrylate, (meth)acrylic acid, 2-methacryloyloxyethyl dihydrogen phosphate, 10-methacryloyloxydecyl dihydrogen phosphate, bis[2-methacryloyloxyethyl] hydrogen phosphate, 4-(2-methacryloyloxyethoxycarbonyl]phthalic acid anhydride (popular name: 4-META), 4-[2-methacryloyloxyethoxycarbonyl]phthalic acid (popular name: 4-MET), 11,11-dicarboxyundecyl(meth)acrylate, 3-methacryloyloxypropyltrimethoxysilane, 2-(N,N-dimethylamino)ethylmethacrylate, and the like. [The term "(meth)acrylate" herein means either methacrylate or acrylate].

Suitable organic peroxides used in the present invention include such known organic peroxides as dibenzoyl peroxide, di-p-chlorobenzoyl peroxide, di-2,4-dichlorobenzoyl peroxide, tertiary butyl peroxybenzoate, methylethyl ketone peroxide, ditertiary butyl peroxide, dicumyl peroxide and cumene hydroperoxide.

In the present invention volatile tertiary alcohols are used as the solvent. The term "volatile" as used herein means "having a boiling point of not more than 200° C. under atmospheric pressure". Suitable alcohols are tert-butanol (b.p. 82.5° C.), tert-pentanol (b.p. 101.8° C.), 3-methyl-3-pentanol (b.p. 126° C.), 3-ethyl-3-pentanol (b.p. 143° C.), 1-methylcyclohexanol (b.p. 155° C.), 2-methyl-2-heptanol (b.p. 156° C.), 3-methyl-3-heptanol (b.p. 159° C.), 4-methyl-4-heptanol (b.p. 161° C.) and the like. One or more of the hydrogen atoms bonded to the carbon atoms of these alcohols may be substituted with a halogen(s) such as Br or Cl or acyl group(s). These tertiary alcohols are used either singly or in admixtures.

The tertiary alcohols may also be used while being mixed with another organic solvent not having radical-polymerizability. In this case, it is preferred that the other organic solvents be mixed in a ratio-less than 1 part by weight based on one part by weight of the tertiary alcohols, and that such other organic solvent be one which does not accelerate the decomposition of the organic peroxide used.

When using the composition of the present invention as a dental primer, the preferred composition ratio is 0.1 to 300 weight parts of the radical-polymerizable monomer and 0.01 to 10 weight parts of the organic peroxide based on 100 weight parts of the diluting solvent.

The primer will also generally contain other ingredients such as polymerization inhibitors, antioxidants, or the like further prevent polymerization in storage. Often photopolymerization initiators are added such as camphorquinone or benzil.

The dental compositions of the present invention are usually supplied in plastic containers. For the purpose of the present invention, the plastics selected should be such that oxygen can permeate through the plastic to thereby prevent the monomer from polymerizing, and the oxygen permeability coefficient should preferably be at least $0.4 \times 10^{-10}$ cm$^2$/sec (cmHg). Suitable such plastics include polyethylene, polypropylene and poly(4-methylpentene-1).

The dental compositions of the present invention can be supplied to the users (dentists and dental technicians) while being packed in a drop-type container having the shape of an eye-lotion container. The required amount of the composition can be removed by simply pinching the container and applied to the surface of a tooth and/or a dental material to be treated. The diluting solvent is allowed to evaporate and a thin coated layer of the composition is formed on the surface.

The dental composition of the present invention is applied as a single-package primer to the surface of the dental metal or the tooth, thereby the metal or the tooth is firmly bonded to other dental materials. The composition can also be used as part of a two-package adhesive, wherein it is mixed with another solution containing a reducing agent (e.g. tertiary amine) capable of generating free radicals upon reaction with an organic peroxide.

The following descriptions are given for illustration of the invention and are not intended to be limiting thereof.

EXAMPLES

Examples 1 through 3 and Comparative Examples 1 through 6

Compositions of Examples 1 through 3 and Comparative Examples 1 through 6 were prepared according to prescriptions shown below using diluting solvents shown in Table 1.

Dental Composition A

| | |
|---|---|
| 2,2-Bis[methacryloyloxypolyethoxyphenyl]propane (commercial name: D-2.6E, made by Shin-Nakamura Chemical Co., Ltd.) | 6 wt. % |
| Neopentyl glycol dimethyacrylate | 3 |
| 10-Methacryloyloxydecyl dihydrogen phosphate | 1 |
| Dibenzoyl peroxide | 1 |
| 2,6-Di-tert-butylhydroxytoluene | 0.02 |
| Diluting solvent | 89.0 |

The following tests 1 and 2 were conducted using the above dental composition A to evaluate the stability of dibenzoyl peroxide and the weight reduction caused by evaporation of the diluting agents.

Test 1

A polypropylene container with a cap (measurements: 20φ×40 mm, wall thickness: 0.5 mm) was filled with 10 cc of Dental Composition A, and the container with the contents were kept at 50° C. for 2 days. The amounts of dibenzoyl peroxide before and after the storage were determined by high-performance liquid chromatography to give the residual ratio of dibenzoyl peroxide after storage of 2 days at 50° C. For the determination, an internal standard of 0.1% biphenyl had been added to Dental Composition A. Table 1 shows the calculation results of the residual ratios.

Test 2

In the same manner as in Test 1, Dental Composition A filled in a plastic container was stored at 50° C. for 2 days, and the weight reduction, caused by evaporation of the diluting solvent which permeated through the polypropylene container, of Composition A was measured. The percentages of weight reduction were calculated and shown in Table 1.

TABLE 1

| | Diluting agent | Residual ratio of dibenzoyl peroxide (wt. %) | Weight Reduction (%) |
|---|---|---|---|
| Example | | | |
| 1 | tert-butanol | 91 | 0 |
| 2 | tert-pentanol | 91 | 0 |
| 3 | 4-methyl-4-heptanol | 92 | 0 |
| Comparative Example | | | |
| 1 | ethanol | 31 | 0 |
| 2 | n-butanol | 37 | 0 |
| 3 | sec-butanol | 24 | 0 |
| 4 | n-butyl acetate | 76 | 8.0 |
| 5 | methyl ethyl ketone | 88 | 4.6 |
| 6 | toluene | 93 | 39 |

Comparative Examples 7 through 9

Dental Compositions A with diluting agent of n-butyl acetate (Comparative Example 7), methyl ethyl ketone (Comparative Example 8) and toluene (Comparative Example 9) were each filled in a 15-cc glass container in a volume of 10 cc, and the containers were stoppered and kept at 50° C. After one day, all three compositions turned white turbid, indicating evidently that the monomer had polymerized.

Obviously, numerous modifications and variations of the present invention are possible in light of the above teachings. It is therefore to be understood that within the scope of the appended claims, the invention may be practiced otherwise than as specifically described herein.

What is claimed as new and deserved to be served by Letters Patent of the United States is:

1. A dental primer or adhesive composition comprising a free radical-polymerizable monomer and an organic peroxide, which are dissolved in a volatile tertiary alcohol, the ratios being 0.1 to 300 weight parts of the monomer and 0.01 to 10 weight parts of the organic peroxide based on 100 weight parts of the tertiary alcohol, said composition being contained in an oxygen-permeable plaster container.

2. The composition of claim 1, wherein said free radical-polymerizable monomer is a (meth)acrylate monomer, said organic peroxide is dibenzoyl peroxide and said tertiary alcohol is tertiary butanol.

3. The composition of claim 1, wherein the monomer is a (meth)acrylate monomer which is conventionally used for a dental material.

4. The composition of claim 1, wherein the monomer is selected from the group consisting of methyl (meth)acrylate, ethyl (meth)acrylate, 2-hydroxyethyl (meth)acrylate, ethylene glycol di(meth)acrylate, neopentyl glycol di(meth)acrylate, triethylene glycol di(meth)acrylate, 2,2-bis[4-(3-methacryloyloxy-2-hydroxypropoxy)phenyl]propane, 2,2-bis[(meth)acryloyoxypolyethoxyphenyl]propane, trimethylolpropane tri(meth)acrylate, (meth)acrylic acid, 2-methacryloyloxyethyl dihydrogen phosphate, 10-methacryloyloxydecyl dihydrogen phosphate, bis[2-methacryloyloxyethyl] hydrogen phosphate, 4-(2-methacryloyloxyethoxycarbonyl]phthalic acid anhydride, 4-[2-methacryloyloxyethoxycarbonyl]phthalic acid, 11,11-dicarboxyundecyl(meth)acrylate, 3-methacryloyloxypropyltrimethoxysilane and 2-(N,N-dimethylamino)ethylmethacrylate.

5. The composition of claim 1, wherein the organic peroxide is selected from the group consisting of dibenzoyl peroxide, di-p-chlorobenzoyl peroxide, di-2,4-dichlorobenzoyl peroxide, tertiary butyl peroxybenzoate, methylethyl ketone peroxide, ditertiary butyl peroxide, dicumyl peroxide and cumene hydroperoxide.

6. The composition of claim 1, wherein the tertiary alcohol is selected from the group consisting of tert-butanol, tert-pentanol, 3-methyl-3-pentanol, 3-ethyl-3-pentanol, 1-methylcyclohexanol, 2-methyl-2-heptanol, 3-methyl-3-heptanol and 4-methyl-4-heptanol.

7. The composition of claim 1, wherein the monomer is selected from the group consisting of methyl (meth)acrylate, ethyl (meth)acrylate, 2-hydroxyethyl (meth)acrylate, ethylene glycol di(meth)acrylate, neopentyl glycol di(meth)acrylate, triethylene glycol di(meth)acrylate, 2,2-bis[4-(3-methacryloyloxy-2-hydroxypropoxy)phenyl]propane, 2,2-bis[(meth)acryloyoxypolyethoxyphenyl]propane, trimethylolpropane tri(meth)acrylate, (meth)acrylic acid, 2-methacryloyloxyethyl dihydrogen phosphate, 10-methacryloyloxydecyl dihydrogen phosphate, bis[2-methacryloyloxyethyl] hydrogen phosphate, 4-(2-methacryloyloxyethoxycarbonyl]phthalic acid anhydride, 4-[2-methacryloyloxyethoxycarbonyl]phthalic acid, 11,11-dicarboxyundecyl(meth)acrylate, 3-methacryloyloxypropyltrimethoxysilane and 2-(N,N-dimethylamino)ethylmethacrylate, and the organic peroxide is selected from the group consisting of dibenzoyl peroxide, di-p-chlorobenzoyl peroxide, di-2,4-dichlorobenzoyl peroxide, tertiary butyl peroxybenzoate, methylethyl ketone peroxide, ditertiary butyl peroxide, dicumyl peroxide and cumene hydroperoxide.

* * * * *

UNITED STATES PATENT AND TRADEMARK OFFICE
CERTIFICATE OF CORRECTION

PATENT NO. : 5,091,441

DATED : February 25, 1992

INVENTOR(S) : Ikuo Omura

It is certified that error appears in the above-identified patent and that said Letters Patent is hereby corrected as shown below:

In the Abstract, lines 4 and 5, read "a plastic contains", should read --a plastic container--;

Column 2, line 57, reads "further prevent", should read --further preventing--;

Column 3, line 8, reads "thin coated", should read --thin-coated--.

Column 4, line 45, reads "permeable plaster container", should read --permeable plastic container--.

Signed and Sealed this

Thirteenth Day of July, 1993

Attest:

MICHAEL K. KIRK

*Attesting Officer*   Acting Commissioner of Patents and Trademarks